US011364022B2

(12) United States Patent
Berges et al.

(10) Patent No.: US 11,364,022 B2
(45) Date of Patent: Jun. 21, 2022

(54) REUSABLE CORE NEEDLE BIOPSY DEVICE AND DISPOSABLE NEEDLE SYSTEM TO ELIMINATE INTERNAL CONTAMINATION RISK IN REUSABLE PORTION OF DEVICE

(71) Applicant: Ithemba, LLC, Baltimore, MD (US)

(72) Inventors: Alexandra Berges, Ellicott City, MD (US); Megan Callanan, Hoboken, NJ (US); Laura Hinson, Spring, TX (US); Madeline Lee, Austin, TX (US); Sophia Triantis, Chevy Chase, MD (US); Valerie Zawicki, Baltimore, MD (US)

(73) Assignee: Ithemba, LLC, Baltimore, MD (US)

( * ) Notice: Subject to any disclaimer, the term of this patent is extended or adjusted under 35 U.S.C. 154(b) by 519 days.

(21) Appl. No.: 16/406,823

(22) Filed: May 8, 2019

(65) Prior Publication Data

US 2019/0343495 A1   Nov. 14, 2019

Related U.S. Application Data

(60) Provisional application No. 62/668,340, filed on May 8, 2018.

(51) Int. Cl.
*A61B 10/02* (2006.01)
*A61B 17/00* (2006.01)

(52) U.S. Cl.
CPC .. *A61B 10/0266* (2013.01); *A61B 2017/0023* (2013.01); *A61B 2560/0443* (2013.01); *A61B 2562/18* (2013.01)

(58) Field of Classification Search
CPC . A61B 10/0041; A61B 10/0291; A61B 10/02; A61B 10/0241; A61B 10/0233;
(Continued)

(56) References Cited

U.S. PATENT DOCUMENTS 3,779,243 A   12/1973   Tussey et al.
4,825,850 A    5/1989   Opie et al.
(Continued)

OTHER PUBLICATIONS

Li et al., "Direct Fabrication of a Hybrid Cell/Hydrogel Construct by a Double-nozzle Assembling Technology", Journal of Bioactive and Compatible Polymers, May 2009, vol. 24, No. 3, pp. 249-265.
(Continued)

*Primary Examiner* — Tse W Chen
*Assistant Examiner* — Avery M Foley
(74) *Attorney, Agent, or Firm* — Jordan IP Law, LLC; Todd A. Vaughn

(57) ABSTRACT

A reusable core biopsy device having a disposable needle assembly to trap and a reusable drive assembly to selectively drive the disposable needle assembly. The disposable needle assembly includes a contamination collection member defining a fluidically-sealed contamination collection chamber to receive and collect contamination during the extraction of the organic tissue sample. The reusable drive assembly includes a locking mechanism to maintain reusable drive assembly in a locked state. An activation member is to place the reusable drive assembly in an unlocked state, to thereby drive, in sequence, the inner needle member and the outer cannula member forward to extract the organic tissue sample.

19 Claims, 10 Drawing Sheets

(58) Field of Classification Search
CPC .............. A61B 10/025; A61B 10/0283; A61B 10/0275; A61B 10/0266; A61B 2562/18; A61B 2560/0443; A61B 17/00234; A61B 2017/0023; A61B 2010/0208; A61B 2010/0225; A61B 2010/0258
See application file for complete search history.

(56) References Cited

U.S. PATENT DOCUMENTS

| | | | |
|---|---|---|---|
| 5,201,908 A | | 4/1993 | Jones |
| 5,284,156 A | | 2/1994 | Schramm et al. |
| 5,546,957 A | | 8/1996 | Heske |
| 5,931,833 A | | 8/1999 | Silverstein |
| 6,083,176 A | | 7/2000 | Terwilliger |
| 6,106,484 A | * | 8/2000 | Terwilliger ........ A61B 10/0233 600/568 |
| 7,041,065 B2 | | 5/2006 | Weilandt et al. |
| 7,753,857 B2 | | 7/2010 | Hibner |
| 8,002,713 B2 | | 8/2011 | Heske et al. |
| 8,172,773 B2 | | 5/2012 | Heske et al. |
| 8,597,205 B2 | | 12/2013 | Seiger et al. |
| 2006/0149127 A1 | | 7/2006 | Seddiqui et al. |
| 2007/0123798 A1 | | 5/2007 | Rahamimov |
| 2008/0091233 A1 | | 4/2008 | Ellis-Behnke et al. |
| 2010/0292673 A1 | | 11/2010 | Korogi et al. |
| 2015/0148615 A1 | * | 5/2015 | Brennan ................ A61B 50/33 600/249 |
| 2015/0148704 A1 | * | 5/2015 | Swick ................ A61B 10/0275 600/567 |
| 2017/0367729 A1 | * | 12/2017 | Ginggen ............ A61B 17/3417 |

OTHER PUBLICATIONS

Huang et al., "Rapid prototyping of a hybrid hierarchical polyurethane-cell/hydrogel construct for regenerative medicine", Materials Science and Engineering: C, Apr. 6, 2013, vol. 33, No. 6, pp. 3220-3229.

Zhao et al., "Three-dimensional printing of Hela cells for cervical tumor model in vitro", Biofabrication, Apr. 11, 2014, vol. 6, No. 3, 10 pages.

Lee et al., "Design and Fabrication of Human Skin by Three-Dimensional Bioprinting", Tissue Engineering: C, Jun. 2014, vol. 20, No. 6, pp. 473-484.

Dai et al., "3D bioprinted glioma stem cells for brain tumor model and applications of drug susceptibility", Biofabrication, Oct. 11, 2016, vol. 8, No. 4, pp. 1-11.

* cited by examiner

REUSABLE CORE NEEDLE BIOPSY DEVICE AND DISPOSABLE NEEDLE SYSTEM TO ELIMINATE INTERNAL CONTAMINATION RISK IN REUSABLE PORTION OF DEVICE

CROSS-REFERENCE TO RELATED APPLICATIONS

The present application claims priority to U.S. Provisional Patent Publication No. 62/668,340 (filed on May 8, 2018), which is hereby incorporated by reference in its entirety.

TECHNICAL FIELD

Embodiments relate to a reusable core biopsy device having a disposable needle system to trap and collect contaminants during the extraction of an organic tissue sample.

BACKGROUND

To diagnose breast cancer, breast tumor tissue is retrieved through a biopsy procedure. There are surgical, fine needle, and core needle biopsy procedures. Core needle biopsy is the gold standard of breast cancer diagnosis. A core needle biopsy device is a minimally invasive tool composed of a thin needle with a cavity to capture tissue and a drive that fires this needle. It is usually used with ultrasound guidance to locate the area of interest. The current technology available are reusable and disposable biopsy devices.

To perform a core needle biopsy procedure using conventional reusable devices, the reusable portion of the device must be opened and a disposable needle is inserted. When the needle is inserted into the patient and fired to extract an organic tissue sample, contaminants travel through the needle and into the internal mechanisms of the reusable portion of the device. The threat of such contamination thus creates a safety hazard, particularly during reuse of the device.

Because a reusable portion of conventional reusable core needle biopsy devices has a significant risk of internal contamination, the device must go through a complicated an inefficient cleaning and sterilization protocol between usages that can take as long as twenty-four hours. This large safety risk and inefficient cleaning procedure discourages physicians and hospitals from using such devices.

Vacuum assisted needle biopsy devices have a closed disposable component that prevents internal contamination of the devices, but are expensive, and thus, cost prohibitive in certain markets.

Another technical problem of reusable devices during a core needle biopsy procedure is undesirable noise generated by the reusable device.

SUMMARY

Embodiments relate to an apparatus to extract an organic tissue sample. Such an apparatus includes a reusable core biopsy assembly and a disposable needle assembly to trap contaminants during the extraction of the organic tissue sample. The apparatus in accordance with embodiments can be manufactured in a simple, efficient, and economic manner.

Embodiments also relate to such an apparatus that is configure to dampen noise during the extraction of an organic tissue sample.

DRAWINGS

Embodiments will be illustrated by way of example in the drawings and explained in the description below.

DESCRIPTION

Figure 1:
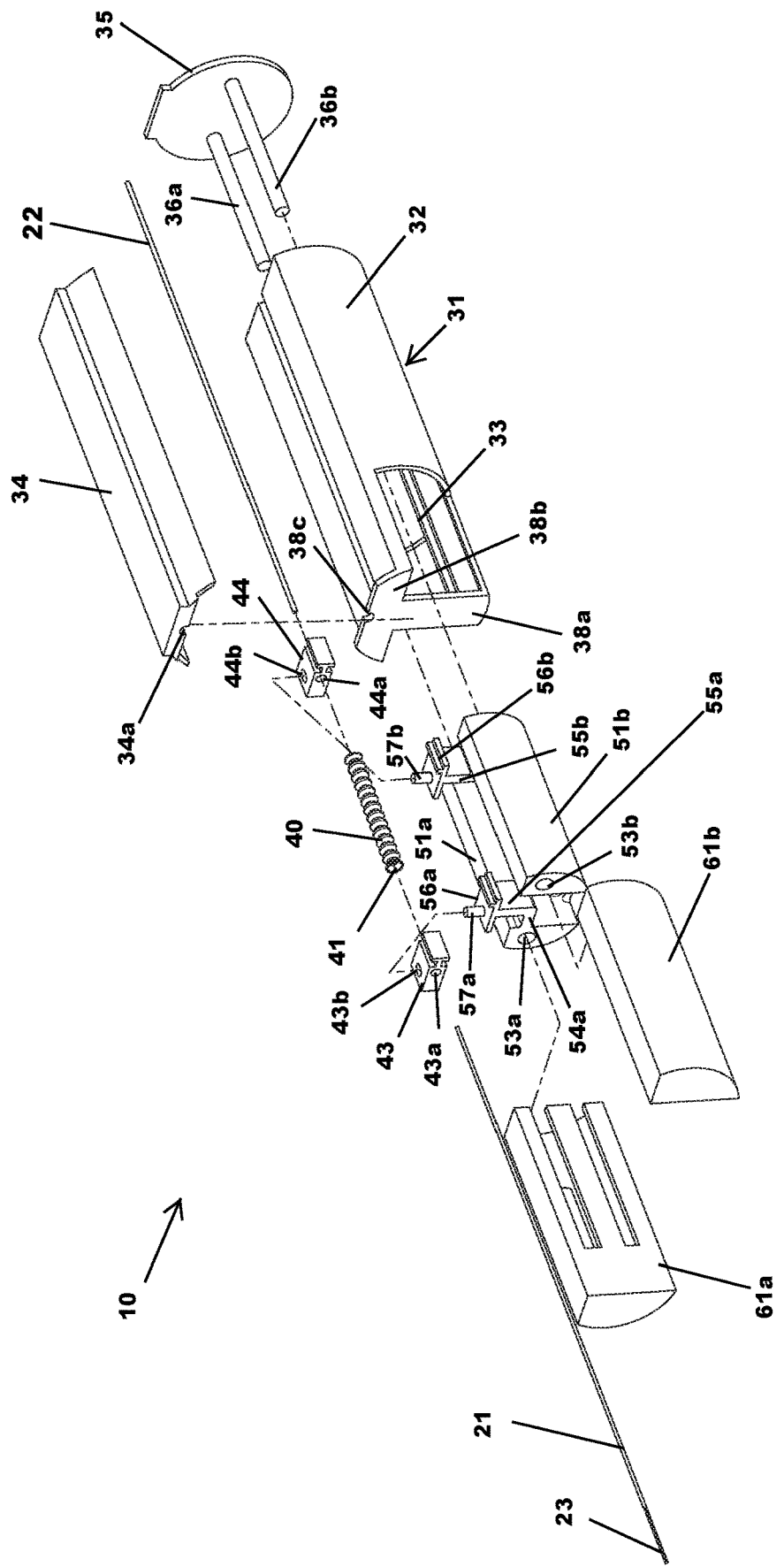
FIG. 1 illustrates an exploded view of an apparatus to extract an organic tissue sample, in accordance with embodiments.
Figure 4:
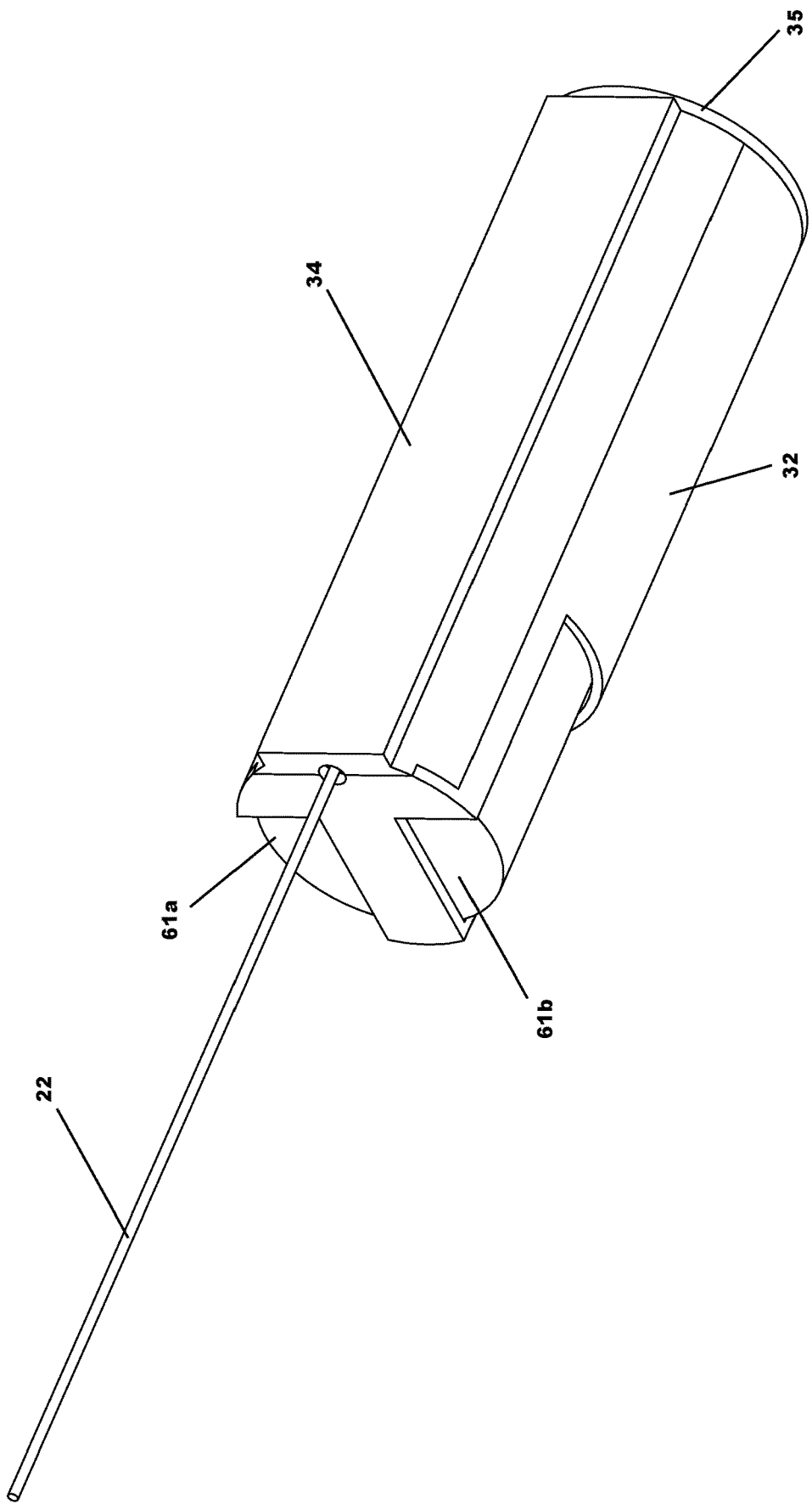
FIG. 4 illustrates a perspective view of the apparatus of FIG. 1, in an assembled or operational state, in accordance with embodiments.

As illustrated in FIGS. 1 and 4, an apparatus 10 to extract an organic tissue sample comprises a disposable needle assembly 20 received by a reusable drive assembly 30 to selectively drive the disposable needle assembly 20 longitudinally between a first operating position in which the needle assembly 20 is loaded (e.g., in a pre-fired state) in the drive assembly 30, and a second operating position in which the disposable needle assembly 20 is driven (e.g., in a fired state) to facilitate the extraction of an organic tissue sample from a patient or specimen.

Needles

The disposable needle assembly 20 comprises an inner needle member 21 and a coaxial outer cannula member 22. The inner needle member 21 has a needle tip 23 and a collection sampling bowl to collect the organic tissue sample upon advancement of the inner needle member 21 into the organic tissue. The outer cannula member 22 has a substantially cylindrical shape or cross-section defining a longitudinal cavity into which the coaxially arranged inner needle member 21 is positioned. The inner needle member 21 and the outer cannula member 22 are independently moveable relative to each other for the extraction of an organic tissue sample. Such movement may occur, for example, telescopically. As further described hereinbelow, during operation, the inner needle member 21 and the coaxial outer cannula member 22 are configured to selectively move or advance in sequence (e.g., within milliseconds of each other). The inner needle member 21 and the outer cannula member 22 may be composed of the same material, such as, for example, a metal or an alloy material. Embodiments, however, are not limited thereto, and thus, the inner needle member 21 and the outer cannula member 22 may be composed of other materials that fall within the spirit and scope of the principles of this disclosure set forth herein.

Contamination Collection Member

Figure 2:
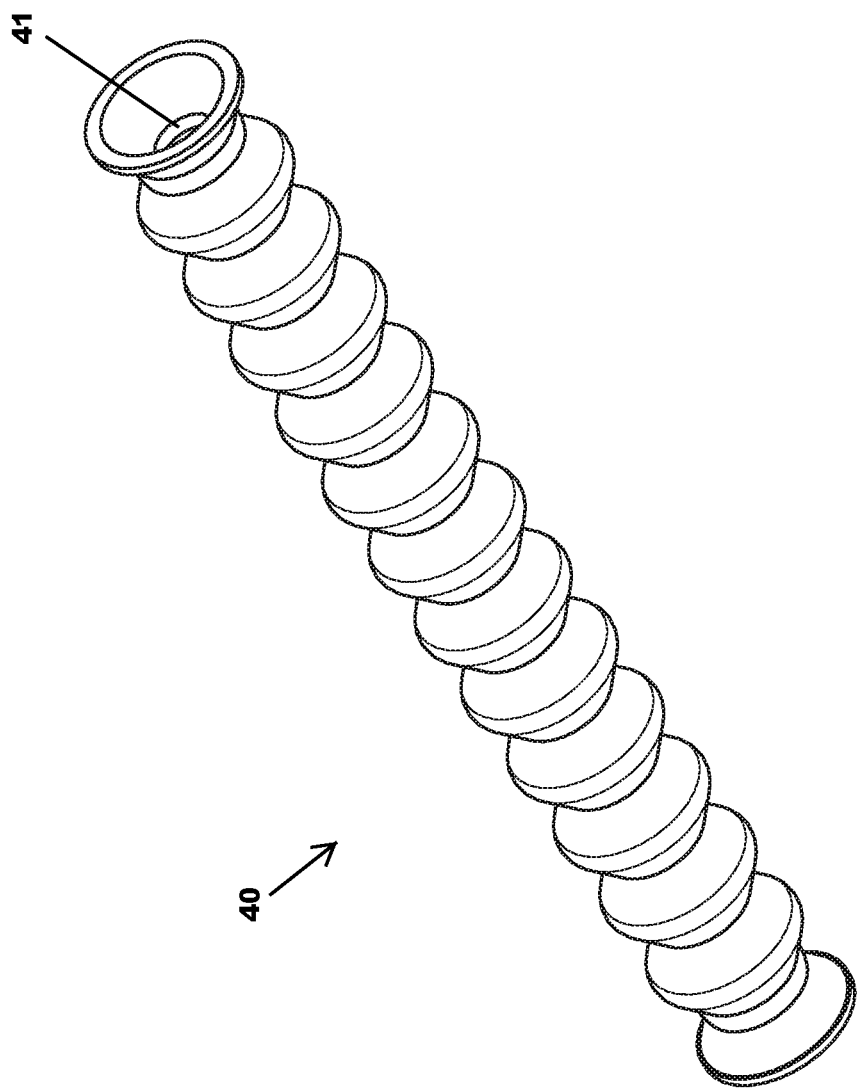
FIG. 2 illustrates a perspective view of the contamination collection member for the apparatus of FIG. 1, in accordance with embodiments.
Figure 3:
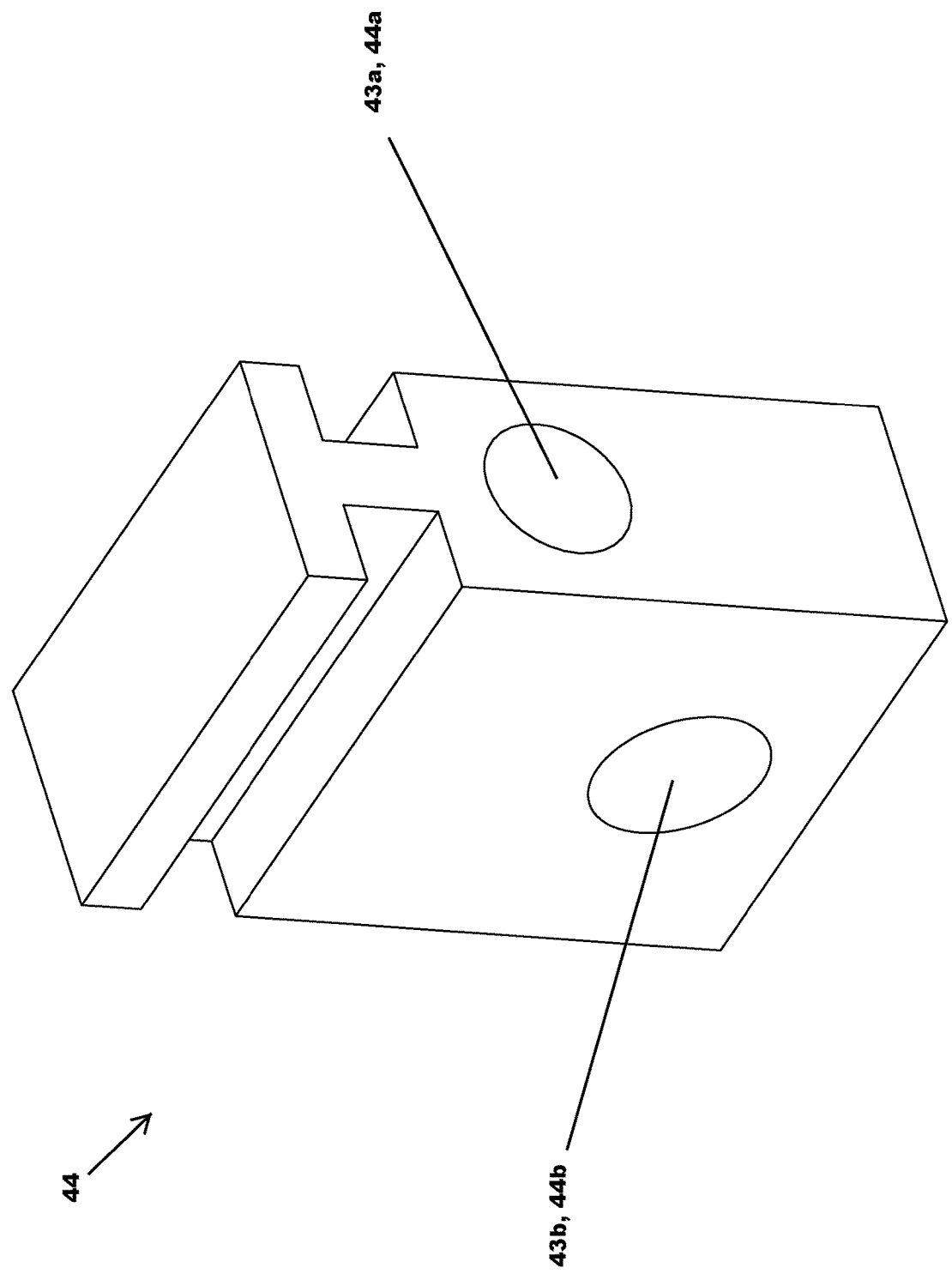
FIG. 3 illustrates a perspective view of a support hub member for the apparatus of FIG. 1, in accordance with embodiments.

As illustrated in FIGS. 2 and 3, a contamination collection member 40 defining a contamination collection chamber 41 structurally configured to receive and collect contamination (e.g., blood) during the extraction of the organic tissue sample. The contamination collection member 40 is operatively connected to the disposable needle assembly 20 via support bracket or hub members 43, 44 positioned respectively at forward and aft regions of the contamination collection member 40.

The support hub members 42 are also configured to fluidically seal the contamination collection chamber 41 at a connecting site or structural interface between the contamination collection member 40 and the support hub members 42. In an example, at the connecting site or structural interface, the distal end regions of the contamination collection member 40 may have one or more of a reduced diameter, a shrink-on connection, or a bonded connection which maintains the fluidic seal of the contamination collection chamber 41. Alternatively or additionally, in an example, such a fluidic seal may be accomplished via a flexible seal member (not illustrated) such as an O-ring.

In accordance with embodiments, the contamination collection member 40 may comprise a flexible and tubular body such as, for example, bellows. The tubular body may be composed of a compressible/expandable, substantially non-permeable, and durable material such as, for example, a polymer material. Embodiments, however, are not limited thereto, and thus, the contamination collection member 40 may encompass other materials that fall within the spirit and scope of the principles of this disclosure set forth herein.

Due to exhibiting such structural flexibility, the contamination collection member 40 is moveable in a direction parallel to the longitudinal axis between a compressed position (e.g., when the apparatus 10 is in a resting or pre-firing state) in which the contamination collection chamber 41 is to have a first volumetric capacity, and an expanded position (e.g., when the apparatus 10 is in a fired state) during the extraction of the organic tissue sample in which the contamination collection chamber 41 is to have a second volumetric capacity that is greater than the first volumetric capacity. Meaning, the volumetric capacity of the contamination collection chamber 41 may correspond to the position of the contamination collection chamber 41.

The contamination collection member 40 is to surround and fluidically seal the inner needle member 21 and the outer cannula member 22 to capture any blood or other contaminants travelling through the coaxial needles during the extraction of an organic tissue sample. Because contaminants are trapped in the contamination collection chamber 41, they cannot enter the reusable drive assembly 30. This facilitates for an easy cleaning procedure and significantly reduces the likelihood of a safety hazard to the patient, user, and/or future patients. The fluidic seal maintained by the contamination collection member 40 permits ingress and egress of air, blood, etc. through the space between the coaxially arranged inner needle member 21 and outer cannula member 22. This facilitates more effective extraction of organic tissue samples.

In accordance with embodiments, the support hub members 42 include a forward support hub member 43 and an aft support hub member 44.

As illustrated in FIG. 3, the forward support hub member 43 includes a first connection opening or aperture 43a extending in a direction substantially parallel to the longitudinal axis to facilitate an operational connection to the inner needle member 21. Such an operational connection is configured to facilitate selective movement of the inner needle member 21 through the first connection aperture 43a in an operating state of the apparatus 10. The forward support hub member 43 also includes a second connection aperture 43b extending in a direction substantially perpendicular to the longitudinal axis to facilitate an operational connection to a left guide member 51a of the drive assembly 30.

The aft support hub member 44 includes a first connection aperture 44a extending in a direction substantially parallel to the longitudinal axis to facilitate an operational connection to the outer cannula member 22. Such an operational connection is configured to facilitate selective movement of the outer cannula member 22 through the first connection aperture 44a in an operating state of the apparatus 10. The aft support hub member 44 also includes a second connection aperture 44b extending in a direction substantially perpendicular to the longitudinal axis to facilitate an operational connection to a right guide member 51b of the drive assembly 30.

Drive Housing

The drive assembly 30 comprises a drive housing 31 into which is at least partially received the needle assembly 20, guide mechanism 50 for receipt in the drive housing 30, a trigger mechanism 60 that includes a left trigger member 61 operatively connected to the left guide members 51a, a locking mechanism 70 to maintain the guide mechanism 50 in a locked state, and an activation member 80 operatively connected to the locking mechanism 70 to selectively fire or activate the apparatus 10.

The drive housing 31 may comprise a bifurcated structural design that includes a housing base 32 defining an interior space 33, a housing cap member 34 that is moveably received on the housing base 32 to cover the interior space 33, and a rear wall member 35 to enclose an exposed rear area of the interior space 33.

Although the illustrated housing base 32 has a substantially cylindrical cross-section, embodiments are not limited thereto, and thus, may encompass other geometric shapes or cross-sections that fall within the spirit and scope of the principles of this disclosure set forth herein. As an example, alternatively or additionally, the bottom outer surface at a rear region of the housing base 32 may comprise one or more ridges having an enhanced gripping surface that permits a user to maintain a grip of the housing base 32 during operation of the apparatus 10. As another example, alternatively or additionally, the bottom outer surface at the rear region of the housing base 32 may extending radially outward to increase the area of the gripping surface that permits a user to maintain a grip of the housing base 32 during operation of the apparatus 10. Due to its reusable nature, the drive housing 31 and components thereof may be composed of a durable and lightweight material such as, for example, metals, metal alloys, polymers, and composites. Embodiments, however, are not limited thereto, and thus, the drive housing 31 and components thereof may be composed of other materials that fall within the spirit and scope of the principles of this disclosure set forth herein.

The housing base 32, at a front region thereof, comprises a front wall 38. The front wall 38 has a T-shaped cross-section that includes a vertically extending member 38a that terminates to a laterally extending cross member 38b. The cross member 38b comprises a cutout 38c of semi-circular cross-section.

A front region of the housing cap member 34 comprises a cutout 34a semi-circular cross-section. The cutout 34a and the corresponding cutout 38c of the housing base 32 are to collectively form a substantially circular opening when the housing cap member 34 is received on the housing base 32. The circular opening is structurally configured to facilitate extension of the inner needle member 21 and the coaxial outer cannula member 22 therethrough for movement during operation of the apparatus 10. Although the illustrated embodiments provide for a housing cap member 34 that is moveably received on the housing base 32, embodiments are not limited thereto, and thus, may encompass other types of structural configurations that permit practice of the embodiments as set forth herein. As an example, the cap member 34 may be pivotally attached to the housing base 32 (e.g., via one or more hinge members) for movement between an open position to expose the interior space 33, and a closed position to cover the interior space 33.

The housing rear wall member 35 may be mechanically connected to the housing base 32. As an example, housing rear wall member 35 may be configured for removable receipt by the housing base 32 via an interference fit. Embodiments, however, are not limited thereto, and thus, the bias mechanism(s) may encompass other types of mechanical connections that fall within the spirit and scope of the principles of this disclosure set forth herein. Embodiments may also encompass a modular structural design in which the housing base 32 and the housing rear wall member 35 are a unitary structure.

The housing rear wall member 35 comprises track members that includes a left track member 36a and a right track member 36b that is positioned spaced apart from the left track member 36a. The track members 36a, 36b are to extend longitudinally in parallel in the interior space 33 in a direction parallel to the longitudinal axis of the housing base 32. Each track member 36a, 36b respectively comprises a rod having concentrically arranged thereon at least one bias mechanism to exert a biasing force in a direction opposite to the rear wall member 35. The bias mechanism(s) may comprise, for example, one or more compression springs. Embodiments, however, are not limited thereto, and thus, the bias mechanism(s) may encompass other types of springs that fall within the spirit and scope of the principles of this disclosure set forth herein.

In an example, the housing base 32 may include a centrally-positioned partition 39 that extends from the surface of the bottom wall in a direction along the longitudinally axis of the housing base 32. The partition 39 may divide the interior space 33 into two separate and substantially symmetric regions defining a left guideway 37a corresponding to the left track member 36a and a right guideway 37b corresponding to the right track member 36b. The interior space 33 is to removably receive the disposable needle assembly 20, the guide members 50, and at least partially, the trigger members 61a, 61b when the apparatus 10 is in an operational state.

Guide Mechanism

Figure 5:
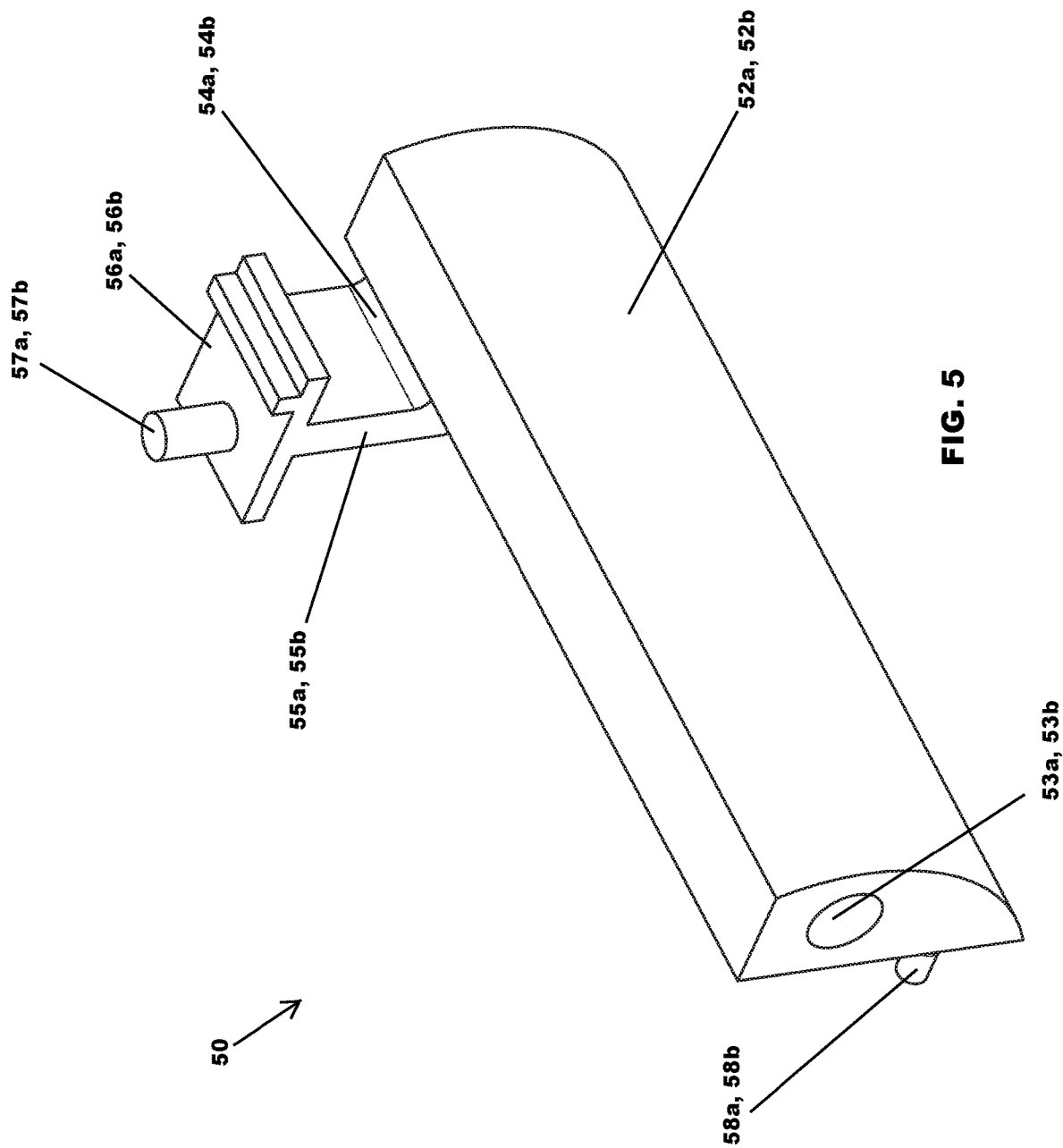
FIG. 5 illustrates a perspective view of the right guide body for the apparatus of FIG. 1, in accordance with embodiments.

As illustrated in FIG. 5, the guide mechanism 50 is configured to guide or otherwise move the disposable needle assembly 20 between the first operating position (locked state) and the second operating position (firing state). The guide mechanism 50 comprises a left guide member 51a configured for selective movement in the corresponding left guideway 37a via left track member 36a, and a right guide member 51b configured for selective movement in the corresponding right guideway 37b via right track member 36b. Due to its reusable nature, the guide mechanism 50 and components thereof may be composed of a durable and lightweight material such as, for example, metals, metal alloys, polymers, and composites. Embodiments, however, are not limited thereto, and thus, the guide mechanism 50 and components thereof may be composed of other materials that fall within the spirit and scope of the principles of this disclosure set forth herein.

The left guide member 51a comprises a left guide member body 52a having a semi-spherical cross-section that corresponds to the cross-section of a corresponding left guideway 37a. The left guide member body 52a comprises a longitudinal extending left guide cavity 53a configured to receive the left track member 36a and thereby align the inner needle member 21 in the interior space 33 when the apparatus 10 is in an operating state.

A support system is arranged at a forward region of the left guide member body 52a to provide support for the inner needle member 21 (or alternatively, the outer cannula member 22) at the forward support hub member 43. The support system comprises a left guide arm member 54a which extends inwardly and substantially laterally from the left guide member body 52a, in a direction substantially perpendicular to the longitudinal axis of the left guide member body 52a.

Extending substantially vertically from the left guide arm member 54a, in a direction substantially perpendicular to the longitudinal axis of the left guide member body 52a, is a left guide leg member 55a having a left platform member 56a provided thereon. A left guide post member 57a extends substantially vertically from the left guide arm member 54a, in a direction substantially parallel to the left guide leg member 55a. The left guide post member 56a is configured to receive the second connection aperture 43c of the forward support hub member 43 to thereby facilitate support of the forward support hub member 43 on the platform member 56a.

Also arranged at a forward region of the support system of the left guide member body 52a is a left locking post member 58a to facilitate a locking state of the left guide member body 52a (as described in further detail hereinbelow). The left locking post member 58a is spatially positioned below the support system, and particularly, the left guide arm member 54a. The left locking post member 58a, which forms part of the locking mechanism 70, extends inwardly and substantially laterally from the left guide member body 52a, where it is to be engaged by a corresponding left hook member 71a of the locking mechanism when the left guide member body 52a is in a locked state. In the locked state, the left guide member body 52a is maintained on the left track member 36a in a position adjacent to otherwise against the rear wall member 35. In this locked state, a bias force exerted by the bias member(s) on the left track member 36a is exerted on the left guide member body 52a. Release of this bias force is to advance the left guide member body 52a forward longitudinally.

Figure 6:
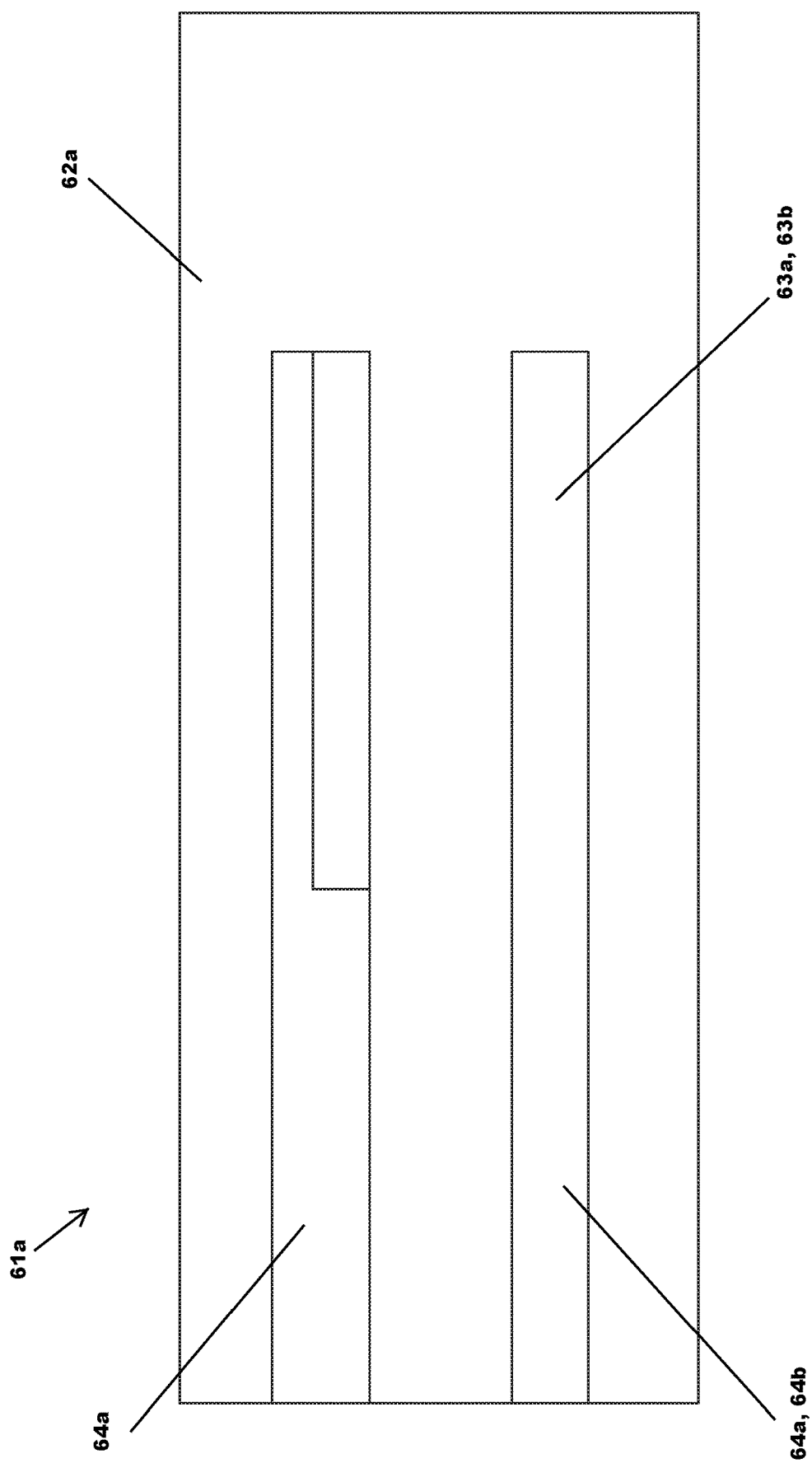
FIG. 6 illustrates a frontal view of a trigger mechanism body for the apparatus of FIG. 1, in accordance with embodiments.

As illustrated in FIG. 6, the right guide member 51b comprises a right guide member body 52b having a semi-spherical cross-section that corresponds to the cross-section of a corresponding right guideway 37b. The right guide member body 52b comprises a longitudinal extending right guide cavity 53b configured to receive the right track member 36b and thereby align the outer cannula member 22 in the interior space 33 when the apparatus 10 is in an operating state.

At an aft or rear region of the right guide member body 52b comprises a support system to provide support for the outer cannula member 22 (or alternatively, the inner needle member 21) at the aft support hub member 44. The support system comprises a right guide arm member 54b which extends inwardly and substantially laterally from the right guide member body 52b, in a direction substantially perpendicular to the longitudinal axis of the right guide member body 52b. Extending substantially vertically from the right guide arm member 54b, in a direction substantially perpendicular to the longitudinal axis of the right guide member body 52b, is a right guide leg member 55b having a right platform member 56b provided thereon. A right guide post member 57b extends substantially vertically from the right guide arm member 54b, in a direction substantially parallel to the right guide leg member 55b. The right guide post member 56b is configured to receive the second connection aperture 44c of the aft support hub member 44 to thereby facilitate support of the aft support hub member 43 on the right platform member 56b.

Also arranged at an aft region of the support system of the right guide member body 52b is a right locking post member 58b to facilitate a locking state of the right guide member body 52b (as described in further detail hereinbelow). The right locking post member 58b is spatially positioned below the support system, and particularly, the right guide arm member 54b. The right locking post member 58b, which forms part of the locking mechanism 70, extends inwardly and substantially laterally from the right guide member body 52b, where it is to be engaged by a corresponding right hook member 71b of the locking mechanism when the right guide member body 52b is in a locked state. In the locked state, the right guide member body 52b is maintained on the right track member 36b in a position adjacent to otherwise against the rear wall member 35. In this locked state, a bias force exerted by the bias member(s) on the right track member 36b is exerted on the right guide member body 52b. Release of this bias force is to advance the right guide member body 52b forward longitudinally.

When the apparatus 10 is in a fully operational state, the support system of each respective guide member 51a, 51b ensures proper spatial alignment between the inner needle member 21 and the outer cannula member 22 when positioned in the housing base 32.

Trigger Members

As illustrated in FIG. 6, the trigger mechanism 60 is configured for selective manipulation by a user to directly engage and move the guide mechanism 50 relative to the drive housing base 32 in a direction parallel to the longitudinal axis of the drive housing base 32. The trigger mechanism 60 comprises a left trigger member 61a operatively connected to the left guide member 51a and a right trigger member 61b operatively connected to the right guide member 51b. Due to its reusable nature, the trigger mechanism 60 may be composed of a durable and lightweight material such as, for example, metals, metal alloys, polymers, and composites. Embodiments, however, are not limited thereto, and thus, the trigger mechanism 60 may be composed of other materials that fall within the spirit and scope of the principles of this disclosure set forth herein.

Figure 7:
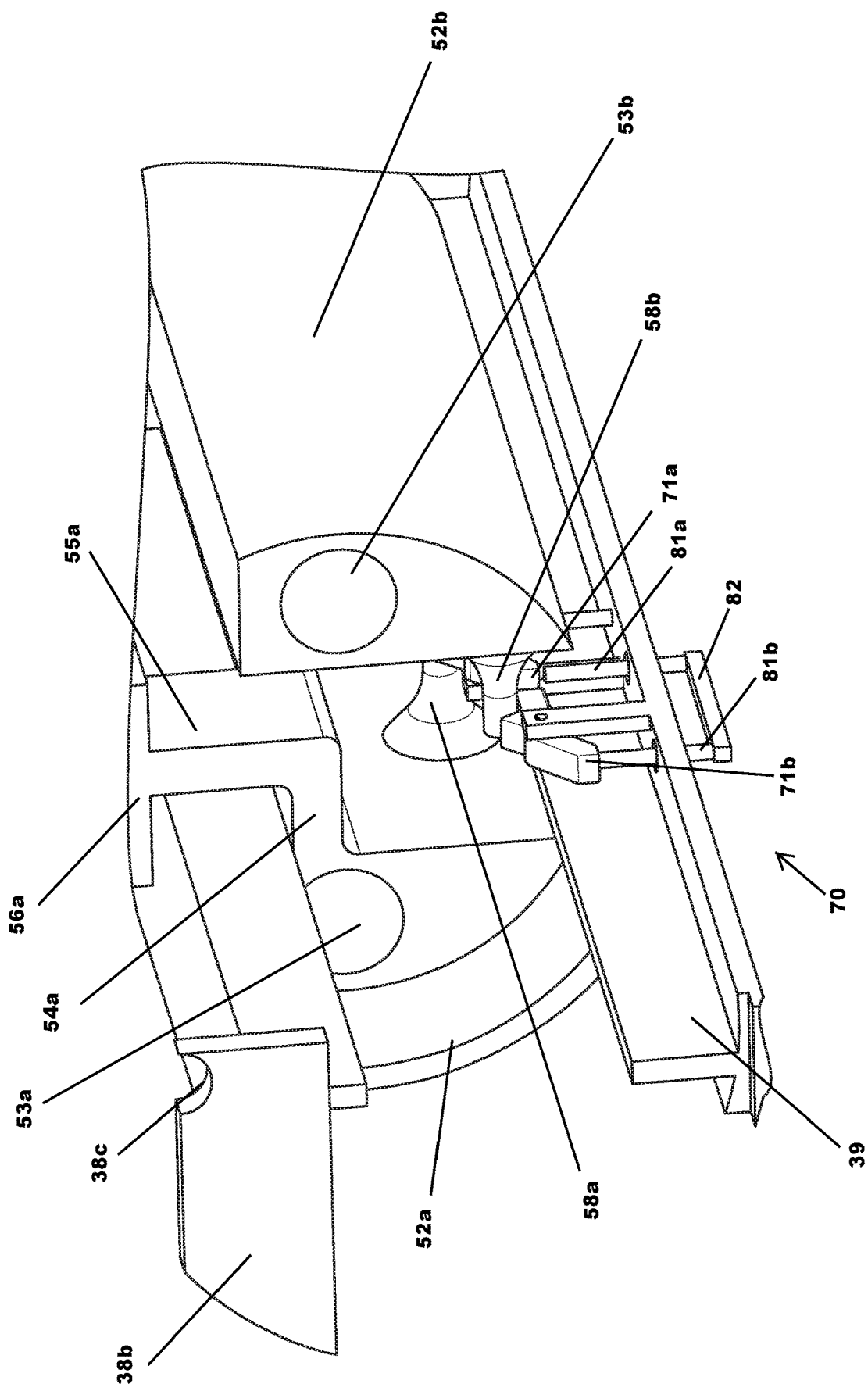
FIG. 7 illustrates a sectional view of the locking mechanism for the apparatus of FIG. 1, in accordance with embodiments.

As illustrated in FIG. 7, the left trigger member 61a comprises left trigger member body 62a having a semi-spherical cross-section that corresponds to the cross-section of a corresponding left guideway 37a and also a corresponding left guide member body 52a. The left trigger member body 62a comprises a longitudinal extending left cavity 63a configured to receive the left guide member body 52a. An interior surface of the left trigger member body 62a includes at least one longitudinal extending left cutout section 64a that corresponds to the left guide arm member 54a in order that it may pass therethrough.

The right trigger member 61b comprises right trigger member body 62b having a semi-spherical cross-section that corresponds to the cross-section of a corresponding right guideway 37b and also a corresponding right guide member body 52b. The right trigger member body 62b comprises a longitudinal extending right cavity 63b configured to receive the right guide member body 52b. An interior surface of the right trigger member body 62b includes at least one longitudinal extending right cutout section 64b that corresponds to the right guide arm member 54b in order that it may pass therethrough.

To dampen noise during the extraction of an organic tissue sample, one or more internal surfaces of each trigger member body 62a, 62b may be provided with a noise-absorbing/filtering material layer configured to absorb or otherwise filter and thereby reduce undesirable external noise during the firing of the apparatus 10. The noise-absorbing/filtering material layer may be composed of one or more of an inorganic glass material and an organic polymer material applied in single or multi-layer form on via a suitable adhesive. As an example, the inorganic glass material may comprise a silicate glass, while the organic polymer may comprise a polymer foam. Embodiments, however, are not limited thereto, and thus, the noise-absorbing/filtering material layer may encompass other materials that fall within the spirit and scope of the principles of this disclosure set forth herein.

Locking Mechanism

Figure 8:
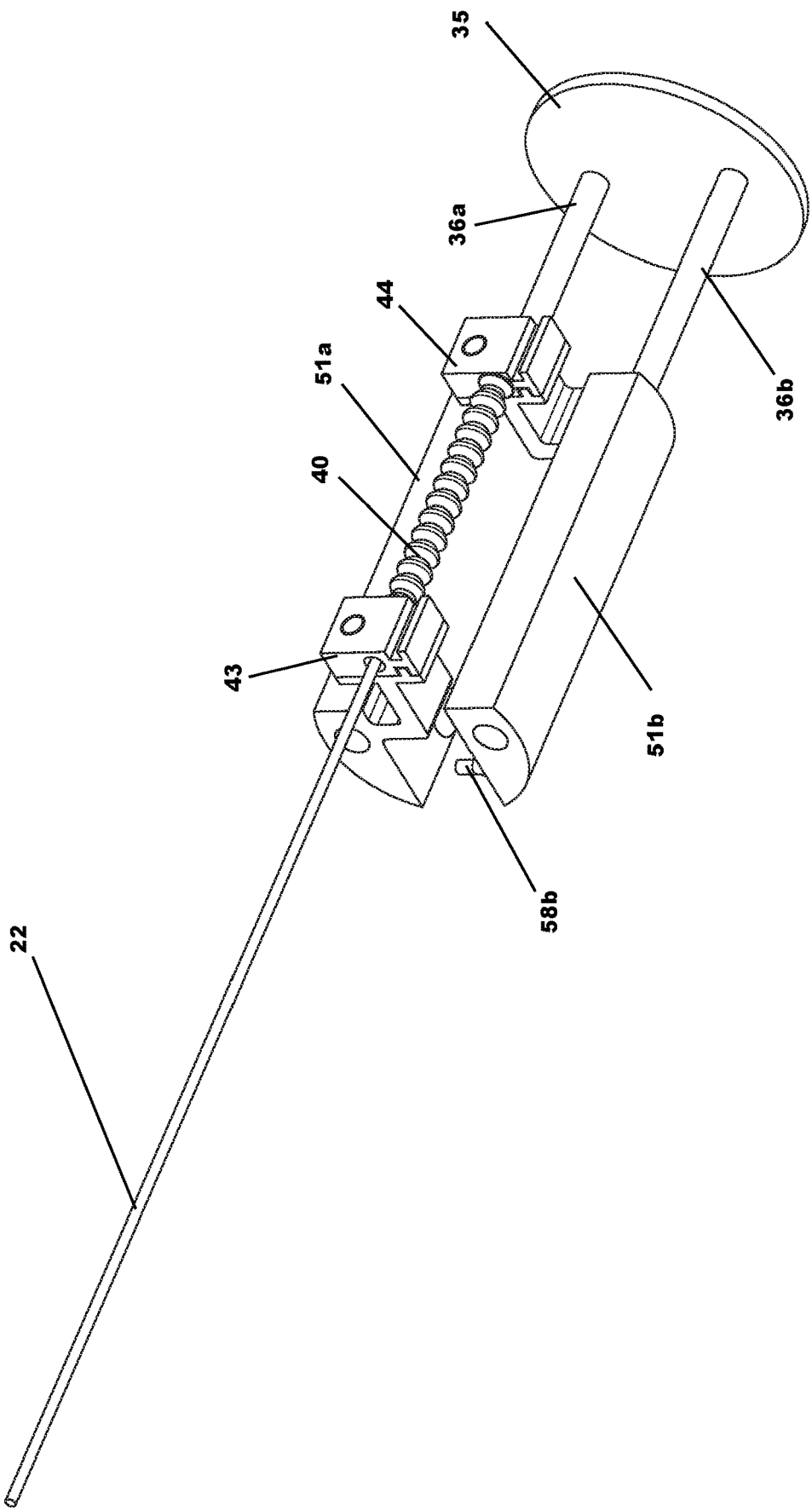
FIG. 8 illustrates a perspective view of view of the guide mechanism and the locking mechanism for the apparatus of FIG. 1, in accordance with embodiments.

As illustrated in FIGS. 7 and 8, the locking mechanism 70 is to maintain the guide members 51a, 51b in a locked state, and includes an aft locking hook 71a and a forward locking hook 71b that are positioned on the bottom surface of the housing base 32 adjacent to the partition 39. To have the necessary delayed sequentially unlocking of the locking mechanism 70, the aft locking hook 71a is to be positioned in the interior space 33 of the drive housing 31 at a location behind (in a frontal view of the apparatus 10) and at a height that is greater than the height of the forward locking hook 71b. The locking hooks 71a, 71b may be composed of a durable material such as, for example, a polymer material. Embodiments, however, are not limited thereto, and thus, the locking hooks 71a, 71b may encompass other materials that fall within the spirit and scope of the principles of this disclosure set forth herein.

The aft locking hook 71a is to selectively engage the left locking post member 58a to maintain the left guide member body 52a in a locked state, and is to selectively disengage the left locking post member 58a in an unlocked state during the firing of the apparatus 10. The aft locking hook 71a is maintained in the locked state by a bias force exerted by one or more left bias mechanism(s) 72a. The left bias mechanism 72a extends between and is connected to the bottom surface of the housing base 32 and a bottom surface of the aft locking hook 71a. The aft locking hook 71a is operatively connected to the bottom surface of the housing base 32 at a left pivot axis 73a, which facilitates the rotation or pivoting of the aft locking hook 71a during movement between the locked state and the unlocked state. The left bias mechanism(s) 72a may comprise, for example, a compression spring. Embodiments, however, are not limited thereto, and thus, the bias mechanism(s) 72a may encompass other types of springs that fall within the spirit and scope of the principles of this disclosure set forth herein.

The forward locking hook 71b is to selectively engage the right locking post member 58b to maintain the right guide member body 52b in a locked state, and is to selectively disengage the right locking post member 58b in an unlocked state during the firing of the apparatus 10. The forward locking hook 71b is maintained in the locked state by a bias force exerted by one or more right bias mechanism(s) 72b. The right bias mechanism 72b extends between and is connected to the bottom surface of the housing base 32 and a bottom surface of the forward locking hook 71b. The forward locking hook 71b is operatively connected to the bottom surface of the housing base 32 at a right pivot axis 73b, which facilitates the rotation or pivoting of the forward locking hook 71b during movement between the locked state and the unlocked state. The right bias mechanism(s) 72b may comprise, for example, a compression spring. Embodiments, however, are not limited thereto, and thus, the right bias mechanism(s) 72b may encompass other types of springs that fall within the spirit and scope of the principles of this disclosure set forth herein.

Activation/Firing Member

As illustrated in FIG. 8, the activation or firing member 80 is operatively connected to the drive housing 30 to selectively fire or activate the needle assembly 20 using the tip of the finger of a user. The activation member 80 is operatively connected to the locking mechanism 70, namely, the aft locking hook 71a and the forward locking hook 71b. The activation member 80 may comprise an activation body that includes a pair of spaced apart activation extension members 81a, 81b connected by an activation cross member 82, and an outer activation shell 83 that covers the activation body and prevents entry of undesirable debris and contaminants. The extension members 81a, 81b are respectively received in openings of a wall of the housing base 32 and into the interior space 33 for connection to the to the locking hooks 71a, 71b.

The activation extension members 81a, 81b and the activation cross member 82 may be composed of a durable and lightweight material such as, for example, metals, metal alloys, polymers, and composites. Embodiments, however, are not limited thereto, and thus, the activation extension members 81a, 81b and the activation cross member 82 may be composed of other materials that fall within the spirit and scope of the principles of this disclosure set forth herein.

The outer activation shell 83 may be composed of a compressible, flexible, and durable material such as, for example, a polymer material. Embodiments, however, are not limited thereto, and thus, the outer activation shell 83 may encompass other materials that fall within the spirit and scope of the principles of this disclosure set forth herein.

Upon pressing of the outer activation shell 83 by a user, the activation cross member 82 initially causes movement of the activation extension member 81a, which in turn, causes the aft locking hook 71a to pivot about the left pivot axis 73a. Such pivoting action thereby causes the left locking post member 58a to disengage from the aft locking hook 71a. The pressing of the outer activation shell 83 also causes the activation cross member 82 to initiate movement of the activation extension member 81b, which in turn, causes the forward locking hook 71b to pivot about the right pivot axis 73b. Such pivoting action thereby causes the right locking post member 58b to disengage from the forward locking hook 71b. In essence, pressing of the outer activation shell 83 by a user selectively moves or advances the locking mechanism to the second locking state by disengaging, in sequence (e.g., within milliseconds) the right locking post member 58b from the forward locking hook 71b and the left locking post member 58a from the aft locking hook 71a.

In Operation

FIGS. 9 to 14 illustrate firing sequences (e.g., open and closed) of the apparatus 10 in order to collect an organic tissue sample.

Figure 9:
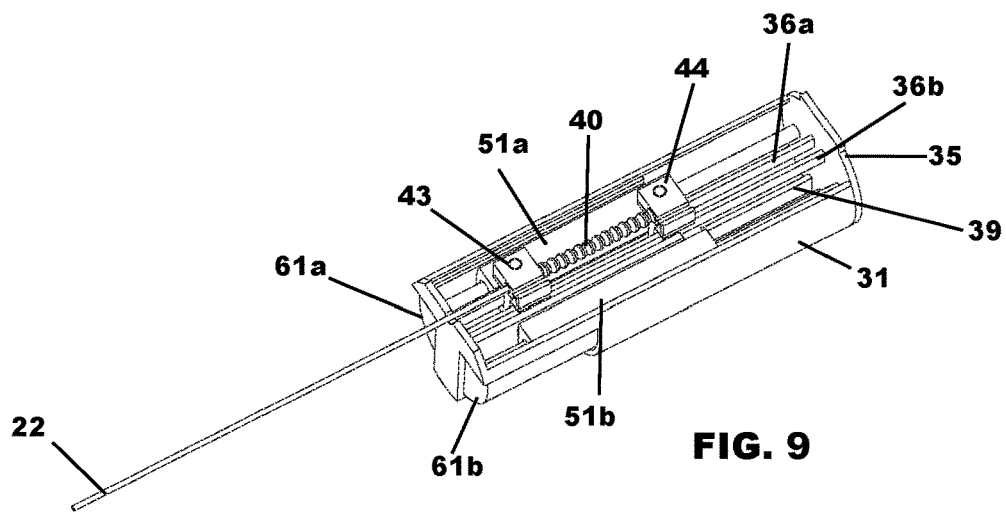
FIGS. 9 to 14 illustrate firing sequences (e.g., open and closed) to collect an organic tissue sample using the apparatus of FIG. 1, in accordance with embodiments.

As illustrated in FIG. 9, in an initial, resting state of the apparatus 10, the trigger members 61a, 61b and corresponding guide members 51a, 51b have not been selectively manipulated by a user into a firing/unlocked position.

Figure 10:
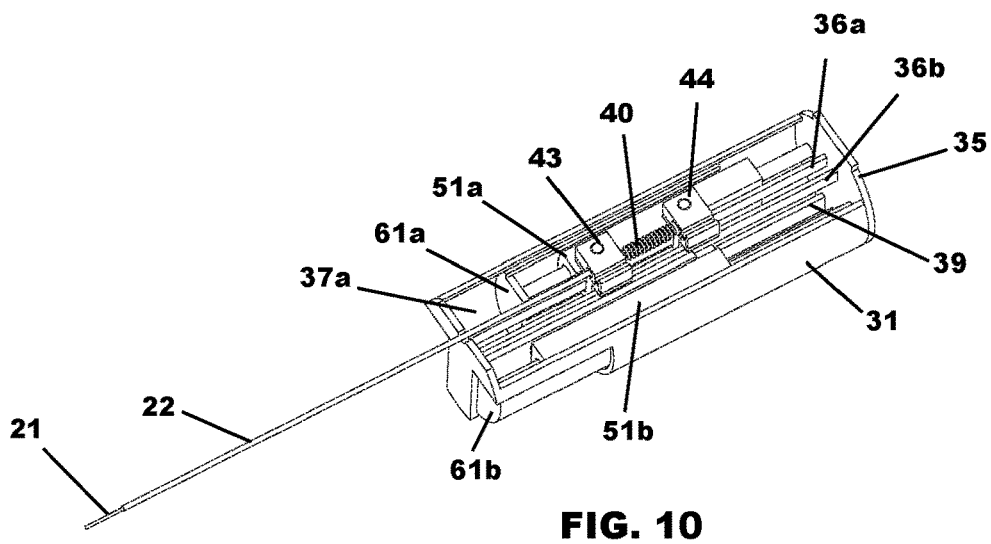

As illustrated in FIG. 10, to expose the collection sampling bowl of the inner needle member 21, the user may manipulate the left trigger member 61a rearwardly in a longitudinal direction toward the housing rear wall 35, which in turn, simultaneously moves the left guide member 51a and the outer cannula member 22 in the same rearward direction. In this operational block, the user is in the process of locking the apparatus 10.

Figure 11:
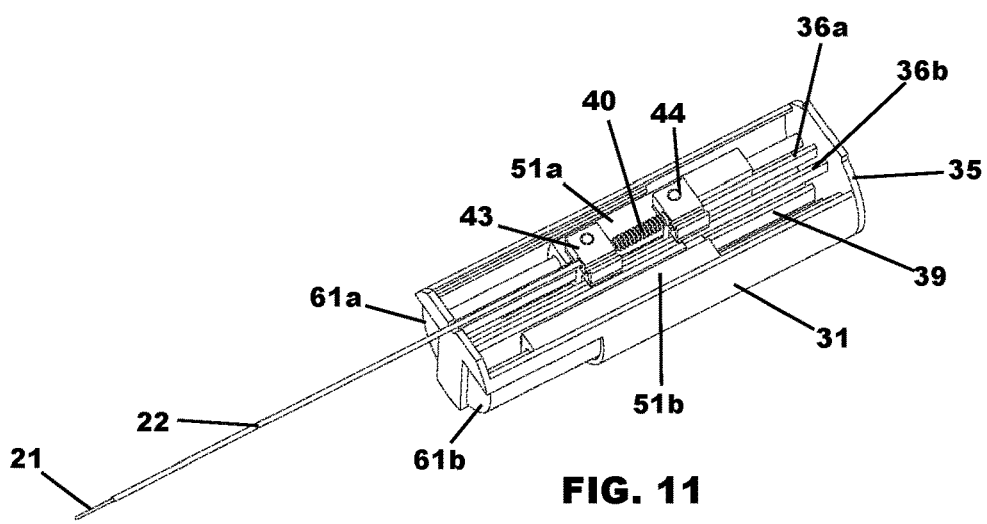

As illustrated in FIG. 11, the user has manipulated the left trigger member 61a forwardly in a longitudinal direction away from the housing rear wall 35, which in turn, serves to lock the left guide member 51a into position by selective engagement of the aft locking hook 71a and the left locking post member 58a. In this position, the left guide member 51a is at rest against the bias force exerted by the bias member(s) on the left track member 36a. Then, the left trigger member 61a is returned to a resting position once the user removes his/her finger(s). The apparatus 10 is now locked in an open firing position, ready to fire upon activation of the activation member 80, which causes the left guide member 51a and the corresponding outer cannula member 22 to move forward and slice the tissue, thereby collecting the organic tissue sample.

Figure 12:
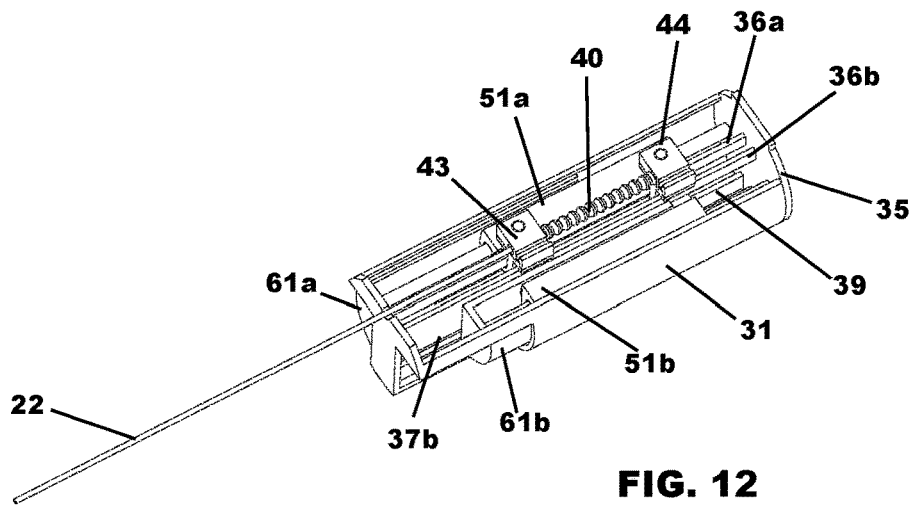

As illustrated in FIG. 12, the user has manipulated the right trigger member 61b rearwardly in a longitudinal direction toward the housing rear wall 35, which in turn, simultaneously moves the right guide member 51b and the inner needle member 21 in the same rearward direction. In this operational block, the user is in the process of locking the apparatus 10.

Figure 13:
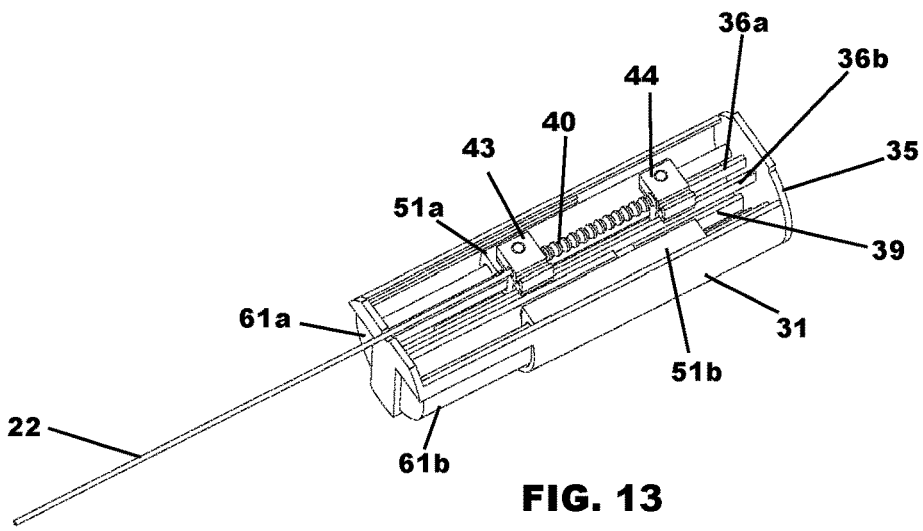

As illustrated in FIG. 13, the user has manipulated the right trigger member 61b forwardly in a longitudinal direction away from the housing rear wall 35, which in turn, serves to lock the right guide member 51b into position by selective engagement of the forward locking hook 71b and the right locking post member 58b. In this position, the right guide member 51b is at rest against the bias force exerted by the bias member(s) on the right track member 36b. Then, the right trigger member 61b is returned to a resting position once the user removes his/her finger(s). The apparatus 10 is now locked in a closed firing position, ready to fire upon activation of the activation member 80.

Figure 14:
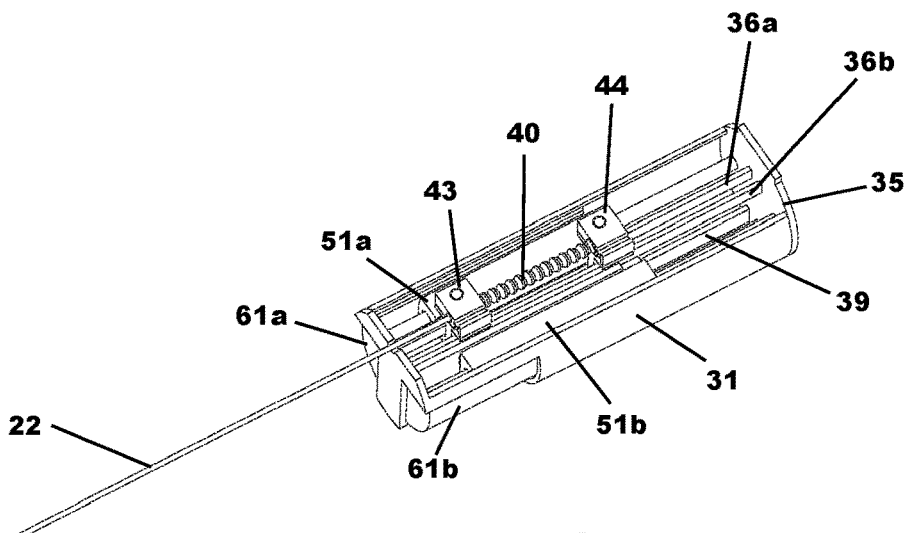

As illustrated in FIG. 14, the user has fired the apparatus 10 by pressing the activation member 80, thereby by selectively disengaging, in a sequence, the forward locking hook 71b and the right locking post member 58b, and then the aft locking hook 71a and the left locking post member 58a. This, in turn, causes forward movement or advancement of the right guide member 51b and the inner needle member 21 (by action of the bias force) initially, to be followed soon thereafter by the left guide member 51a and the outer cannula member 22 (by action of the bias force). This sequential motion by the inner needle member 21 and the outer cannula member 22 causes the outer cannula member 22 to perform a cutting or slicing action on the organic tissue, thereby collecting an organic tissue sample in the collection sampling bowl of the inner needle member 21. The apparatus 10 has returned to its initial resting position with nothing locked in place.

Additional Notes and Examples

Example 1 may include an apparatus to extract an organic tissue sample, the apparatus comprising: a disposable needle assembly, including an inner needle member and an outer cannula member that is coaxially arranged relative to the inner needle member, and a contamination collection member defining a fluidically sealed contamination collection chamber to receive and collect contamination during the extraction of the organic tissue sample; and a reusable drive assembly to selectively drive the disposable needle assembly between a first operating position to maintain the guide mechanism in a locked state against a bias force, and a second operating position to drive the inner needle member and the outer cannula member forward, in sequence, via the bias force, to extract the organic tissue sample, wherein the contamination collection member is moveable between a compressed position in which, during the first operating position, the contamination collection chamber is to have a first volumetric capacity, and an expanded position during the extraction of the organic tissue sample in which, during the second operating position, the contamination collection chamber is to have a second volumetric capacity that is greater than the first volumetric capacity.

Example 2 may include the apparatus of Example 1, further comprising a drive housing having a first track member and a second track member extending in parallel from a rear wall of the drive housing; a guide mechanism, operatively connected to the drive housing, including a first guide member body operatively connected to the inner needle member and a second guide member body operatively connected to the outer cannula member; a locking mechanism, operatively connected to the drive housing, including a first locking member to engage and maintain the first guide member body in the locked state, and a second locking member to engage and maintain the first guide member body in the locked state; and an activation member, operatively connected to the drive housing, to disengage and release, in sequence, the first guide member body and the second guide member body from the locked state.

Example 3 may include the apparatus of Example 2, further comprising a forward support hub member to fluidically seal the contamination collection member at a forward end thereof, the forward support hub member including a longitudinal connection aperture for operational connection to the inner needle member, and a vertical connection aperture for operational connection to the guide members.

Example 4 may include the apparatus of Example 3, further comprising an aft support hub member to fluidically seal the contamination collection member at an aft end thereof, the aft support hub member including a longitudinal connection aperture for operational connection to the outer cannula member, and a vertical connection aperture for operational connection to the guide members.

Example 5 may include the apparatus of Example 2, wherein the first guide member body comprises: a first guide cavity to receive one of the track members; a first support system to support the forward support hub member; and a first locking post member to engage the first locking member in the locked state of the first guide member body.

Example 6 may include the apparatus of Example 5, further comprising a first trigger member body having a cavity configured to receive the first guide member body such that, when selectively manipulated by a user, causes rearward longitudinal movement of the first guide member body relative to the drive housing to thereby cause engagement between the first locking post member and the first locking member; and a noise-absorbing material layer on one or more internal surfaces of the first trigger member body to reduce external noise during the firing of the apparatus.

Example 7 may include the apparatus of Example 2, wherein the second guide member body comprises: a second guide cavity to receive one of the track members; a second support system to support the aft support hub member in a manner that spatially aligns the inner needle member and the outer cannula member; and a second locking post member to engage the second locking member in the locked state of the second guide member body.

Example 8 may include the apparatus of Example 7, further comprising a second trigger member body having a cavity configured to receive the second guide member body such that, when selectively manipulated by a user, causes rearward longitudinal movement of the second guide member body relative to the drive housing to thereby cause engagement between the second locking post member and the second locking member; and a noise-absorbing material layer on one or more internal surfaces of the second trigger member body to reduce external noise during the firing of the apparatus.

Example 9 may include an apparatus to extract an organic tissue sample, the apparatus comprising: an inner needle member and a coaxial outer cannula member, each operatively connected to a contamination collection member defining a fluidically sealed contamination collection chamber to receive and collect contamination during the extraction of the organic tissue sample; and a reusable drive assembly including: a first guide member body operatively connected to the inner needle member; a second guide member body operatively connected to the outer cannula member; a first locking mechanism to maintain the first guide member body in a locked state; a second locking mechanism to maintain the second guide member body in a locked state; and an activation member operatively connected to the first locking mechanism and the second locking mechanism, to place the first guide member body and the second guide member body in an unlocked state, in sequence, to thereby drive, in sequence, the inner needle member and the outer cannula member forward to extract the organic tissue sample.

Example 10 may include the apparatus of Example 9, wherein the contamination collection member is moveable between a compressed position in which the contamination collection chamber has a first volumetric capacity, and an expanded position in which the contamination collection chamber is to have a second volumetric capacity that is greater than the first volumetric capacity.

Example 11 may include the apparatus of Example 10, wherein the contamination collection member is in: the compressed position during the locked state of the first guide member body and the second guide member body, and the expanded position during the unlocked state of the first guide member body and the second guide member body.

Example 12 may include the apparatus of Example 9, wherein the reusable drive assembly comprises a drive housing having a first track member and a second track member extending in parallel from a rear wall of the drive housing.

Example 13 may include the apparatus of Example 12, further comprising a forward support hub member to fluidically seal the contamination collection member at a forward end thereof, the forward support hub member including a longitudinal connection aperture for operational connection to the inner needle member, and a vertical connection aperture for operational connection to the guide members.

Example 14 may include the apparatus of Example 13, further comprising an aft support hub member to fluidically seal the contamination collection member at an aft end thereof, the aft support hub member including a longitudinal connection aperture for operational connection to the outer cannula member, and a vertical connection aperture for operational connection to the guide members.

Example 15 may include the apparatus of Example 12, wherein the first guide member body comprises: a first guide cavity to receive one of the track members; a first support system to support the forward support hub member; and a first locking post member to engage the first locking member in the locked state of the first guide member body.

Example 16 may include the apparatus of Example 15, further comprising a first trigger member body having a cavity configured to receive the first guide member body such that, when selectively manipulated by a user, causes rearward longitudinal movement of the first guide member body relative to the drive housing to thereby cause engagement between the first locking post member and the first locking member; and a noise-absorbing material layer on one or more internal surfaces of the first trigger member body to reduce external noise during the firing of the apparatus.

Example 17 may include the apparatus of Example 12, wherein the second guide member body comprises: a second guide cavity to receive one of the track members; a second support system to support the aft support hub member in a manner that spatially aligns the inner needle member and the outer cannula member; and a second locking post member to engage the second locking member in the locked state of the second guide member body.

Example 18 may include the apparatus of Example 17, further comprising a second trigger member body having a cavity configured to receive the second guide member body such that, when selectively manipulated by a user, causes rearward longitudinal movement of the second guide member body relative to the drive housing to thereby cause engagement between the second locking post member and the second locking member; and a noise-absorbing material layer on one or more internal surfaces of the second trigger member body to reduce external noise during the firing of the apparatus.

Example 19 may include an apparatus to drive a disposable needle assembly that includes including an inner needle member and a coaxial outer cannula member, the apparatus comprising: a first guide member body operatively connected to the inner needle member; a second guide member body operatively connected to the outer cannula member; a first locking mechanism to maintain the first guide member body in a locked state; a second locking mechanism to maintain the second guide member body in a locked state; and an activation member to engage, in sequence, the first locking mechanism and place the first guide member body in an unlocked state, and then the second locking mechanism and place the second guide member body in an unlocked state, and thereby drive, in sequence, the inner needle member and the outer cannula member forward to extract the organic tissue sample.

The terms "coupled," "attached," or "connected" may be used herein to refer to any type of relationship, direct or indirect, between the components in question, and may apply to electrical, mechanical, fluid, optical, electromagnetic, electromechanical or other connections. In addition, the terms "first," "second," etc. are used herein only to facilitate discussion, and carry no particular temporal or chronological significance unless otherwise indicated.

As used in this application and in the claims, a list of items joined by the term "one or more of" or "at least one of" may mean any combination of the listed terms. For example, the phrases "one or more of A, B or C" may mean A; B; C; A and B; A and C; B and C; or A, B and C. In addition, a list of items joined by the term "and so forth", "and so on", or "etc." may mean any combination of the listed terms as well any combination with other terms.

Those skilled in the art will appreciate from the foregoing description that the broad techniques of the embodiments may be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

LIST OF REFERENCE SYMBOLS

10 Apparatus
20 Disposable needle assembly
21 Inner needle member
22 Outer cannula member
23 Needle tip (inner needle member)
30 Drive assembly
31 Drive Housing
32 Housing base
33 Interior space
34 Housing cap member
34a Cutout (housing cap member)
35 Housing rear wall
36a Left track member
36b Right track member
37a Left guideway
37b Right guideway
38 Front wall (housing base)
38a Vertically extending member (front wall)
38b Cross member (front wall)
38c Cutout (housing base)
39 Partition (Housing base)
40 Contamination collection member
41 Chamber (contamination collection member)
42 Support hub members
43 Forward support hub member
43a First connection aperture (Forward support hub member)
43b Second connection aperture (Forward support hub member)
44 Aft support hub member
44a First connection aperture (Aft support hub member)
44b Second connection aperture (Aft support hub member)
50 Guide mechanism
51a Left guide member
51b Right guide member
52a Left guide member body
52b Right guide member body
53a Left guide cavity
53b Right guide cavity
54a Left guide arm member
54b Right guide arm member
55a Left guide leg member
55b Right guide leg member
56a Left platform member 56b Right platform member
57a Left guide post member
57b Right guide post member
58a Left locking post member
58b Right locking post member
60 Trigger mechanism
61a Left trigger member
61b Right trigger member
62a Left trigger member body
62b Right trigger member body
63a Left cavity
63b Right cavity
64a Left cutout section
64b Right cutout section
70 Locking mechanism
71a Left hook member
71b Right hook member
72a Left bias mechanism
72b Right bias mechanism
73a Left pivot axis
73b Right pivot axis
80 Activation mechanism
81a Aft activation extension member
81b Forward activation extension member
82 Activation cross member
83 Outer activation shell

What is claimed is:

1. An apparatus to extract an organic tissue sample, the apparatus comprising:
a disposable needle assembly, including an inner needle member and an outer cannula member that is coaxially arranged relative to the inner needle member, a contamination collection member defining a fluidically sealed contamination collection chamber to receive and collect contamination during the extraction of the organic tissue sample, a forward support hub member to fluidically seal the contamination collection member at a forward end thereof, the forward support hub member including a longitudinal connection aperture for operational connection to the inner needle member, and a vertical connection aperture; and
a reusable drive assembly to selectively drive the disposable needle assembly between a first operating position to maintain the disposable needle assembly in a locked state against a bias force, and a second operating position to drive the inner needle member and the outer cannula member forward, in sequence, via the bias force, to extract the organic tissue sample, the reusable drive assembly including a guide mechanism, operatively connected to a drive housing, including a first guide member body operatively connected to the inner needle member and the vertical connection aperture, and a second guide member body operatively connected to the outer cannula member,
wherein the contamination collection member is moveable between a compressed position in which, during the first operating position, the contamination collection chamber is to have a first volumetric capacity, and an expanded position during the extraction of the organic tissue sample in which, during the second operating position, the contamination collection chamber is to have a second volumetric capacity that is greater than the first volumetric capacity.

2. The apparatus of claim 1, wherein the reusable drive assembly comprises:
the drive housing having a first track member and a second track member extending in parallel from a rear wall of the drive housing;
a locking mechanism, operatively connected to the drive housing, including a first locking member to engage and maintain the second guide member body in the locked state, and a second locking member to engage and maintain the first guide member body in the locked state; and
an activation member, operatively connected to the drive housing, to disengage and release, in sequence, the first guide member body and the second guide member body from the locked state.

3. The apparatus of claim 2, further comprising an aft support hub member to fluidically seal the contamination collection member at an aft end thereof, the aft support hub member including a longitudinal connection aperture for operational connection to the outer cannula member, and a vertical connection aperture for operational connection to the first guide member body.

4. The apparatus of claim 3, wherein the second guide member body comprises:
a second guide cavity to receive one of the track members;
a second support system to support the aft support hub member in a manner that spatially aligns the inner needle member and the outer cannula member; and
a second locking post member to engage the second locking member in the locked state of the second guide member body.

5. The apparatus of claim 4, further comprising a second trigger member body having a cavity configured to receive the second guide member body such that, when selectively manipulated by a user, causes rearward longitudinal movement of the second guide member body relative to the drive housing to thereby cause engagement between the second locking post member and the second locking member; and a noise-absorbing material layer on one or more internal surfaces of the second trigger member body to reduce external noise during firing of the apparatus.

6. The apparatus of claim 2, wherein the first guide member body comprises:
a first guide cavity to receive one of the track members;
a first support system to support the forward support hub member; and
a first locking post member to engage the first locking member in the locked state of the first guide member body.

7. The apparatus of claim 6, further comprising a first trigger member body having a cavity configured to receive the first guide member body such that, when selectively manipulated by a user, causes rearward longitudinal movement of the first guide member body relative to the drive housing to thereby cause engagement between the first locking post member and the first locking member; and a noise-absorbing material layer on one or more internal surfaces of the first trigger member body to reduce external noise during firing of the apparatus.

8. An apparatus to extract an organic tissue sample, the apparatus comprising:
a contamination collection member defining a fluidically sealed contamination collection chamber to receive and collect contamination during the extraction of the organic tissue sample;
an inner needle member and a coaxial outer cannula member, each operatively connected to the contamination collection member;

a forward support hub member to fluidically seal the contamination collection member at a forward end thereof, the forward support hub member including a longitudinal connection aperture for operational connection to the inner needle member, and a vertical connection aperture; and a reusable drive assembly including: a first guide member body operatively connected to the inner needle member; a second guide member body operatively connected to the outer cannula member; a first locking mechanism to maintain the first guide member body in a locked state; a second locking mechanism to maintain the second guide member body in a locked state; and an activation member operatively connected to the first locking mechanism and the second locking mechanism, to place the first guide member body and the second guide member body in an unlocked state, in sequence, to thereby drive, in sequence, the inner needle member and the outer cannula member forward to extract the organic tissue sample.

9. The apparatus of claim 8, wherein the contamination collection member is moveable between a compressed position in which the contamination collection chamber has a first volumetric capacity, and an expanded position in which the contamination collection chamber is to have a second volumetric capacity that is greater than the first volumetric capacity.

10. The apparatus of claim 9, wherein the contamination collection member is in:
the compressed position during the locked state of the first guide member body and the second guide member body, and
the expanded position during the unlocked state of the first guide member body and the second guide member body.

11. The apparatus of claim 8, wherein the reusable drive assembly comprises a drive housing having a first track member and a second track member extending in parallel from a rear wall of the drive housing.

12. The apparatus of claim 11, further comprising an aft support hub member to fluidically seal the contamination collection member at an aft end thereof, the aft support hub member including a longitudinal connection aperture for operational connection to the outer cannula member, and a vertical connection aperture for operational connection to the first guide member body.

13. The apparatus of claim 12, wherein the second guide member body comprises:
a second guide cavity to receive one of the track members;
a second support system to support the aft support hub member in a manner that spatially aligns the inner needle member and the outer cannula member; and
a second locking post member to engage the second locking mechanism in the locked state of the second guide member body.

14. The apparatus of claim 13, further comprising a second trigger member body having a cavity configured to receive the second guide member body such that, when selectively manipulated by a user, causes rearward longitudinal movement of the second guide member body relative to the drive housing to thereby cause engagement between the second locking post member and the second locking mechanism; and a noise-absorbing material layer on one or more internal surfaces of the second trigger member body to reduce external noise during firing of the apparatus.

15. The apparatus of claim 11, wherein the first guide member body comprises:
a first guide cavity to receive one of the track members;
a first support system to support the forward support hub member; and
a first locking post member to engage the first locking mechanism in the locked state of the first guide member body.

16. The apparatus of claim 15, further comprising a first trigger member body having a cavity configured to receive the first guide member body such that, when selectively manipulated by a user, causes rearward longitudinal movement of the first guide member body relative to the drive housing to thereby cause engagement between the first locking post member and the first locking mechanism; and a noise-absorbing material layer on one or more internal surfaces of the first trigger member body to reduce external noise during firing of the apparatus.

17. A reusable apparatus to drive a disposable needle assembly that includes an inner needle member and a coaxial outer cannula member, the apparatus comprising:
a drive housing including a housing base defining an interior space;
a first guide member body received in the interior space and operatively connected to the inner needle member for selective movement between a locked state and an unlocked state, the first guide member body having an inner needle member support system at a forward region thereof to support the inner needle member, the inner needle member support system including a first guide arm member and a first guide leg member extending from the first guide arm member;
the first guide arm member extends inwardly and substantially laterally from the first guide member body, in a direction substantially perpendicular to a longitudinal axis of the first guide member body; and the first guide leg member extends substantially vertically from the first guide arm member, in a direction substantially perpendicular to the longitudinal axis of the first guide member body;
a second guide member body received in the interior space and operatively connected to the outer cannula member for selective movement between a locked state and an unlocked state, the second guide member body having an outer cannula member support system at an aft region thereof to support the outer cannula member, the outer cannula member support system including a second guide arm member and a second guide leg member extending from the second guide arm member;
a first locking mechanism to maintain the first guide member body in the locked state in the drive housing;
a second locking mechanism to maintain the second guide member body in a-the locked state in the drive housing; and
an activation member operatively connected to the drive housing to engage, in sequence, the first locking mechanism and place the first guide member body in the unlocked state, and then the second locking mechanism and place the second guide member body in the unlocked state, and thereby drive, in sequence, the inner needle member and the outer cannula member forward to extract an organic tissue sample.

18. The reusable apparatus of claim 17, wherein:
the second guide arm member extends inwardly and substantially laterally from the second guide member body, in a direction substantially perpendicular to a longitudinal axis of the second guide member body; and the second guide leg member extends substantially vertically from the second guide arm member, in a direction substantially perpendicular to the longitudinal axis of the second guide member body.

19. The reusable apparatus of claim 17, wherein:

the first guide member body includes a first platform member provided on the first guide leg member, and a first guide post member, extending substantially vertically from the first platform member in a direction substantially parallel to the first guide leg member, configured to facilitate support of the inner needle member; and the second guide member body includes a second platform member provided on the second guide leg member, and a second guide post member, extending substantially vertically from the second platform member in a direction substantially parallel to the second guide leg member, configured to facilitate support of the outer cannula member.

\* \* \* \* \*